Figure 1A:
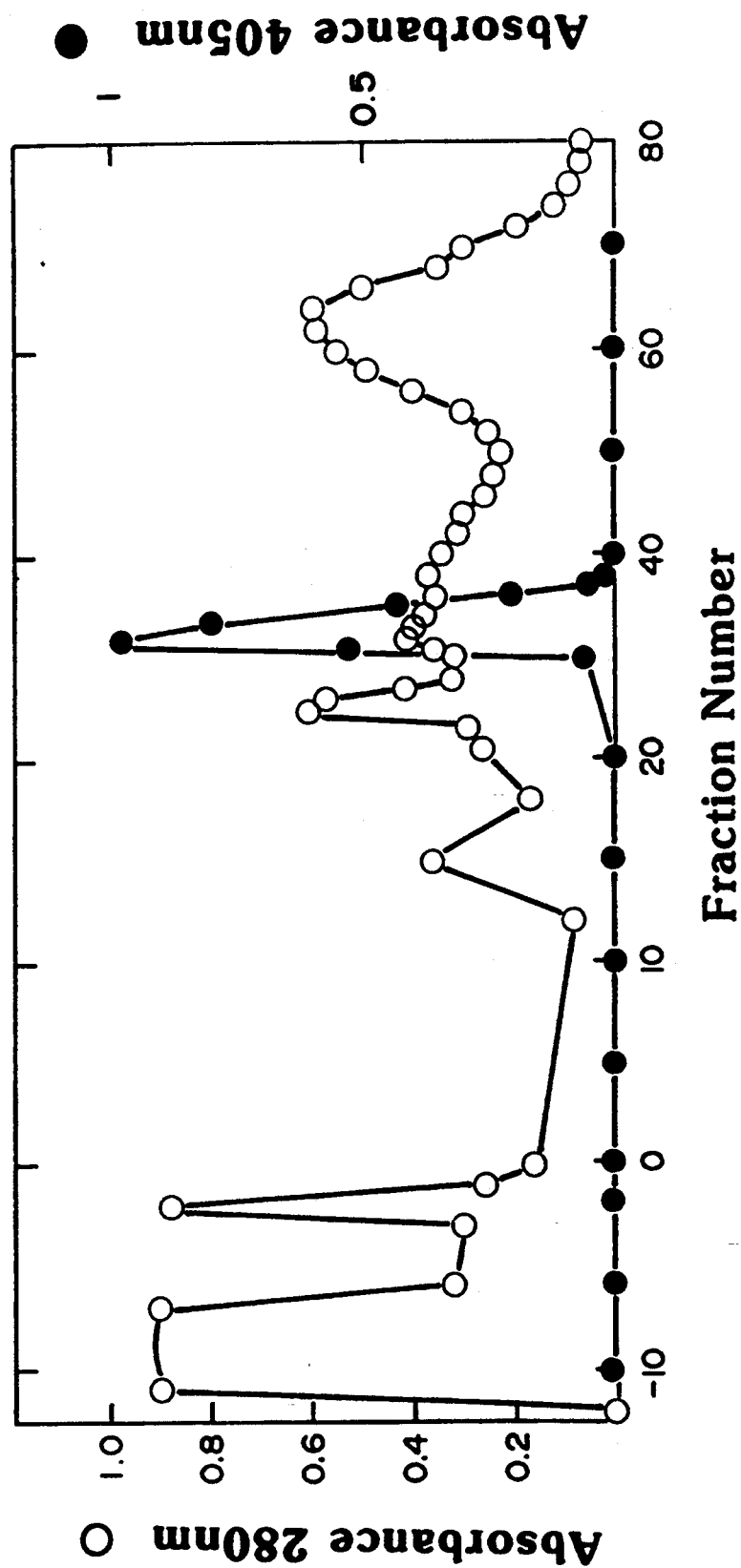

United States Patent [19]
Chelladurai et al.

[11] Patent Number: 5,378,607
[45] Date of Patent: Jan. 3, 1995

[54] METHOD FOR TESTING FOR THE PRESENCE OF METASTATIC TUMOR CELLS

[75] Inventors: Mohanathasan Chelladurai, Southfield; Kenneth V. Honn, Grosse Pointe Woods; Daniel A. Walz, Detroit, all of Mich.

[73] Assignee: Biomide Investment Limited Partnership, Grosse Pointe Farms, Mich.

[21] Appl. No.: 737,431

[22] Filed: Jul. 29, 1991

[51] Int. Cl.⁶ .................. G01N 33/53; G01N 33/574; G01N 33/86
[52] U.S. Cl. .................................. 435/7.23; 435/7.24; 435/7.2; 435/13; 435/960; 435/7.33; 435/7.34; 436/501; 436/63; 436/64; 436/813
[58] Field of Search ....................... 435/7.23, 7.24, 7.2, 435/13, 960, 7.33, 7.34; 436/501, 63, 64, 813

[56] References Cited

PUBLICATIONS

Natali, P. G., et al, PNAS, vol. 86, No. 17, pp. 6719–6723 (1989).
Johnson, J. P., et al, Invasion Metastasis, vol. 9, pp. 338–350 (1989).
Herlyn, M., et al., Leuk. Res., vol. 8, No. 3, pp. 323–334 (abstract only) 1984.

*Primary Examiner*—Toni R. Scheiner
*Attorney, Agent, or Firm*—Ian C. McLeod

[57] ABSTRACT

A method of testing for the presence of tumor cells which are metastatic based upon the presence of Human Leukocyte Antigen (HLA) is described. In the test a protein which selectively binds the HLA is used to determine the presence of excess HLA which is a characteristic of the tumor cells. The preferred protein is a bacterial enterotoxin, preferably the enterotoxin A (SEA) produced by *Staphylococcus aureus*.

14 Claims, 5 Drawing Sheets

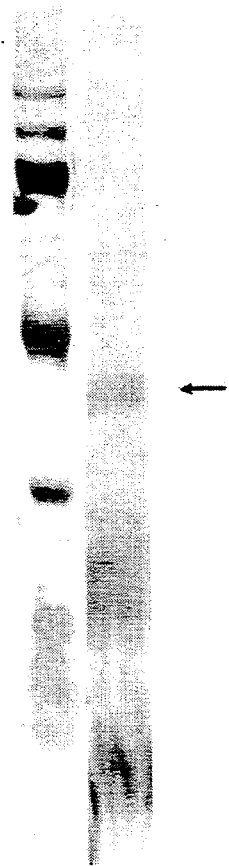
a b
FIG. IC

H$_2$N – Ile – Lys – Glu – Glu – His – Val – Ile – Ile – Gln – Ala – Glu – Phe – – – (A)

H$_2$N – Ile – Lys – Glu – Glu – His – Val – Ile – Ile – Gln – Ala – Glu – Phe – – – (B) – – Ref 22

METHOD FOR TESTING FOR THE PRESENCE OF METASTATIC TUMOR CELLS

BACKGROUND OF THE INVENTION

(1) Field of the Invention

The present invention relates to a method for testing for the presence of metastatic human tumor cells by determining the level of Human Leukocyte Antigen (HLA) in the tumor cells. In particular the present invention relates to a method which uses a bacterial toxin or subunit thereof which selectively binds the HLA to provide a basis For the detection and level of activity.

(2) Prior Art

In 1865, Trousseau observed a high incidence of venous thrombosis in patients with gastric carcinoma and described the syndrome which bears his name (Trousseau, A., In Clinique Medicale de l'Hotel-Dieu de Paris; Paris, Balliere, 3:654 (1865)). A considerable body of evidence supports an association between cancer and thromboembolic disorders (Rickles, F. R., et al., Blood 62:14-31 (1983)) and elements of the hemostatic system (i.e. platelets, thrombin and fibrin) are proposed as causal for tumor cell metastasis (Weiss, L., et al., Clin. Expl. Metas. 7:127-167 (1989)). Activated platelets may enhance tumor cell adhesion to the vessel wall (Honn, K. V., et al., Biochem. Pharm. 34:235-241 (1985)) and induce endothelial cell retraction (Honn, K. V., et al., FASEB. J. 3:2285-2293 (1989)) while fibrin may aid tumor cells to escape the cellular immune system (Gorelik, E., Cancer Res. 47:809-815 (1987)). Tumor cell activation of platelets and generation of fibrin may require thrombin. Therefore, the identification and isolation of the tumor cell prothrombogenic protein(s) responsible for thrombin generation are of considerable interest.

At least four separate factors are thought to mediate tumor cell induced thrombin generation. The first is tissue factor, a transmembrane glycoprotein and receptor, also associated with normal tissue (Broze, G. J., et al., J. Biol. Chem. 260:10917-10920 (1985); and Buha, A., et al., Proc. Natl. Acad. Sci. USA 83:299-302 (1986)). The second, cancer procoagulant, is a cysteine proteinase that directly activates factor X (Gordon, S. G., et al., J. Clin. Invest. 67:1665-1671 (1981)). The third is a protein termed platelet aggregating activity/procoagulant activity (PAA/PCA) isolated from solid tumors or from tumor cells grown in culture which lacks proteolytic activity and is dependent upon factor X for activity (Cavanaugh, P. G., et al., Thromb. Res. 37:309-326 (1985)). More recently, a factor Xa receptor has been identified on some tumor cells (Sakai, T., et al., J. Biol. Chem. 265:9105-9113 (1990)).

It is important to know if solid tumors are metastatic. If the tumor is not metastatic then the tumor can be removed. If the tumor cell is metastatic then various forms of radical surgery, chemotherapy and radiation may be indicated. It is important that there be a reliable test for metastatic tumor cells.

OBJECTS

It is therefore an object of the present invention to provide a reliable test which detects when particular tumor cells are metastatic. In particular the presentation provides a test which is simple and economical. These and other objects will become increasingly apparent by reference to the following description and the drawings.

IN THE DRAWINGS

FIG. 1a shows the results of Q-Sepharose column chromatography of material from human ovarian tumors which were metastatic. The plasma membrane fraction containing 0.25% CHAPS (3-cholamidopropyldimethyl-amminio-1-propane sulfonate) was applied onto a 1 cm×30 cm column equilibrated in 25 mM Tris-HCl buffer, pH 7.5, containing 0.25% CHAPS. The column was washed with two column volumes of starting buffer to remove unbound protein and developed with a 0.0-1.0M NaCl gradient in 120 ml at a flow rate of 60 ml/hr. The eluate was fractionated into 5 ml volumes. Absorbance at 280 nm is shown as open circles. Procoagulant activity is shown as closed circles. As shown in FIG. 1a, the activity eluted in a symmetric peak. The active fractions were pooled, dialyzed against 10 mM $KH_2PO_4/K_2HPO_4$ buffer, pH 7.2 and applied onto a hydroxyapatite column (Source: Bio-Rad, Rockville, N.Y.). Activity was detected in the protein fraction which did not bind to this column. The active sample was then delipidated as described hereinafter. Finally, the protein preparation was dialyzed and applied onto a Mono Q column as shown in FIG. 1b.

Figure 1B:
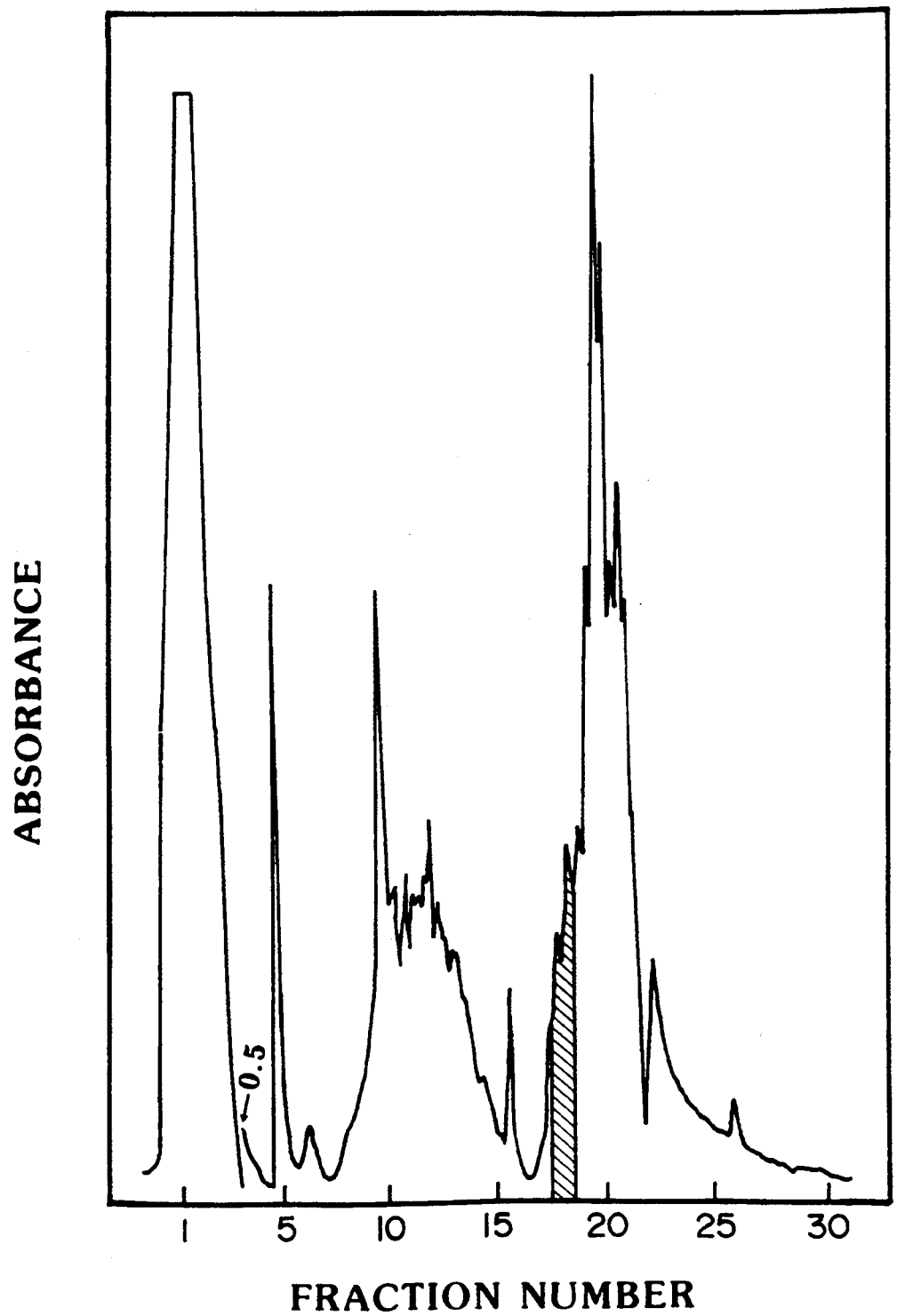

FIG. 1b shows the Mono Q column chromatography. The column was equilibrated in 25 mM Tris-HCl buffer, pH 8.2. Protein isolated from the hydroxyapatite column was delipidated. There was therefore no further requirement for detergents in this and subsequent steps. The column was washed with two column volumes to remove unbound protein and developed with a 0.0-1.0M NaCl gradient in 120 ml at a flow rate of 60 ml/hr. The eluate was fractionated into 5 ml volumes. Most activity (~75%) was seen in fraction 18 (shaded area). It was obvious that the activity resided in the ascending portion of another major protein peak. Some activity was also present in fractions 19 through 23 but they were not included, thus reducing contaminating proteins.

FIG. 1c shows the slab gel electrophoretic pattern of the procoagulant protein preparation after the Mono Q column chromatography of FIG. 1b in the presence of sodium dodecyl sulfate (lane a) and beta-mercaptoethanol (lane b). Slab gel electrophoresis with SDS was carried out according to Laemmli (Laemmli, U. K., Nature (London). 227:680-685 (1970)). Stacking and separating gels were 4% and 9% acrylamide, respectively. Samples were diluted 1:2 in the upper gel buffer containing 2% (w/v) SDS and heated to 100° C. for 5 minutes. Gels were fixed and stained with 0.25% Coomassie blue in 50% methanol and 10% acetic acid. The protein band of 35,000 daltons (arrowed) was excised and sequenced. Another band of 28,000 was also observed but not sequenced. Molecular weight markers beta-galactosidase (116,000), phosphorylase a (94,000), bovine serum albumin (68,000), ovalbumin (43,000) and carbonic anhydrase (29,000) are shown in lane a.

Figures 2, 4:
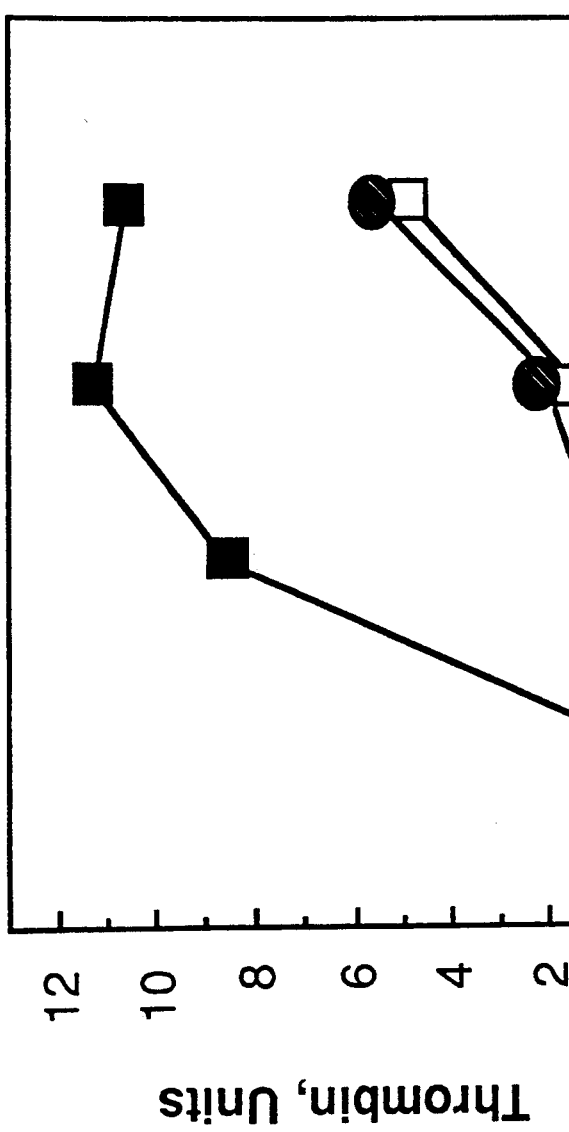

FIG. 2 shows a comparison of the amino-terminal sequence of the first 12 residues of the 35,000 dalton protein isolated from Human Ovarian Carcinoma (A) with that of the HLA-DR protein (B: see Kappes, D, et al., Ann. Rev. Biochem. 57:991-1028 (1988)). It was concluded that these proteins were similar.

Figure 3A:
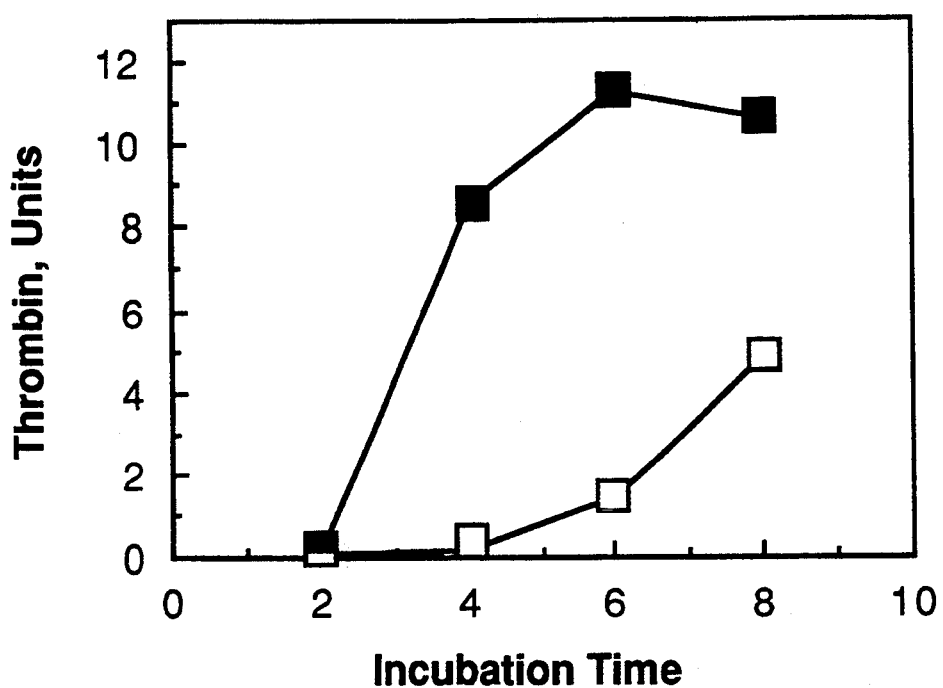
Figure 3B:
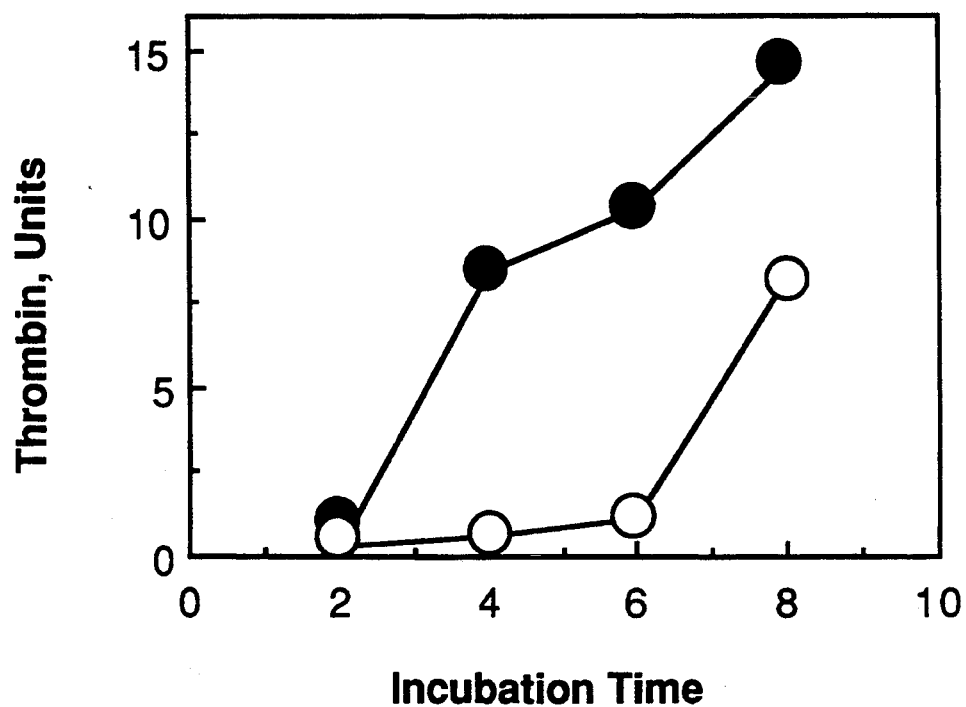

FIGS. 3A and 3B show a time course of thrombin generation in normal human plasma (3A) and plasma deficient in Factor VII (3B) in the presence (closed symbols) and absence (open symbols) of HLA-DR. The concentration of HLA-DR was 115 nM (Read, S. M., et al., Anal. Biochem. 116:53-64 (1981)). These results are representative of ten different experiments using three different preparations of immunoaffinity purified HLA-DR and show that HLA-DR causes thrombin generation.

FIG. 4 shows the effect of Staphylococcal enterotoxin A on procoagulant activity of HLA-DR. Experiments were carried out exactly as described in FIG. 10 except that normal plasma was preincubated with HLA-DR ■, HLA-DR and SEA ●, or with nothing which was the control. SEA completely inhibited the HLA-DR.

GENERAL DESCRIPTION

The present invention relates to a method for testing cells for the presence of human tumor cells which are metastatic which comprises testing a sample of human cells, suspected of containing human tumor cells which are metastatic to determine the presence of Human Leukocyte Antigen (HLA), wherein the tumor cells exhibit higher HLA activity as compared to HLA activity in normal human cells. The cells are preferably from human blood serum.

Further the present invention relates to a method for testing cells for the presence of human tumor cells which are metastatic which comprises testing cells of human tissue suspected of containing human tumor cells which are metastatic with a protein which selectively binds Human Leukocyte Antigen (HLA) to determine the presence of the tumor cells, wherein the tumor cells exhibit higher HLA activity as compared to HLA activity in normal human cells as determined by the binding of the HLA with the protein.

The proteins which are preferred are toxins which bind HLA. The toxins are selected from the group consisting of Staphylococcus aureus endotoxin A, B, C1, C2, C3, D and E, Toxic Shock Syndrome bacterial toxin, Streptococcus pyrogenes A and C, Staphylococcus aureus exfoliating toxins A and B as well as active subunits of these toxins which selectively bind the HLA. Preferred is S. aureus toxin A (SEA).

The toxins are used in an amount which binds the HLA, preferably between about 1 and 10 arbitrary units (AU) per unit of HLA. Generally a solution containing between about 1 and 10 AU/ml of the toxin is used to inhibit the HLA. The toxins preferably selectively bind HLA-DR.

The test can be in a blood coagulation assay, where the HLA is inhibited by the toxin; in a titration assay using the toxin which is metered into a sample of the HLA with an end point indicator; in an immunoassay with an antibody which is specific for HLA using various known techniques. All of these types of assays are well known to those skilled in the art.

In the preferred assay in blood plasma where the metastatic tumor cells are in the plasma, blood plasma is freed of fibrinogen by forming a fibrin clot which is separated from the plasma. The inhibition of HLA generated thrombin in the plasma is then detected using varying amounts of the toxin added to the tumor cells or to the HLA isolated from the cells. Larger amounts of HLA in metastatic cells requires larger amounts of toxin to slow the rate of thrombin generation. The thrombin is detected using a colorimetric assay.

The inhibition of HLA induced coagulation by the toxin can also be tested as a function of the clotting time using the tumor cells with or without the toxin. Such types of assays are well known to those skilled in the art. Preferably a control is run with normal plasma as well.

The samples can be isolated from the solid tumors of various types including ovarian carcinoma cells, melanomas and small cell carcinoma of the lung. If the tumor cells show excess levels of HLA over the normal cells, they are determined to be metastatic.

The gene products of the Major Histocompatibility Complex (MHC) are some of the main proteins involved in the ability of cells to respond to foreign antigens. Of the two classes, the Class I proteins are known as the transplantation antigens while the Class II proteins are referred to as the immune response proteins (Kappes, D, et al., Ann. Rev. Biochem. 57:991-1028 (1988)). Structural studies have revealed that each class of protein exists as an alpha-beta heterodimer on the surface of a variety of cell types including leukocytes, lymphocytes, macrophages and monocytes. In the human the alpha and beta chains of class II heterodimer have molecular weights of 33,000 and 28,000, respectively (Lee, J. S., et al., Nature. 299:750-752 (1982)). It has been found that the 35,000 and 28,000 dalton proteins of HLA-DR isolated either by conventional methods or by immunoaffinity chromatography enhanced thrombin generation in normal plasma. Authentic HLA-DR also had procoagulant activity and thus strengthened these observations. Interestingly, the 35,000 and 28,000 proteins individually express procoagulant activity when electrophoresed on SDS-PAGE followed by Western blot transfer to immobilon P membrane (transfer to this membrane ensures removal of sodium dodecyl sulfate which permits not only sequence analysis but also testing in the bioassay). This finding suggests that the alpha-beta heterodimer complex is not a prerequisite for procoagulant activity. The alpha chain shares 35% homology with the beta chain (Lee, J. S., et al., Nature. 299:750-752 (1982)), thus it is believed that these areas of sequence homology contain the peptides with the procoagulant activity. Both the alpha and beta chains span the membrane. Each chain consists of two main extracellular domains of 90-100 amino acids, a transmembrane region of 20-25 amino acids and an intracellular segment of 8-15 amino acid residues. The procoagulant activity is present in intact tumor cells (Chelladurai, M., et al., Proc. Am. Ass. Can. Res. 29:68a (1988)) suggesting that the procoagulant activity resides with the extracellular moiety of the HLA-DR molecule. Further strength is given to this from the observation that intact T cells specifically bind radiolabelled staphylococcal enterotoxin A (SEA). The procoagulant activity of HLA-DR is completely inhibited by SEA which is specific to HLA-DR.

There are three subsets of the Class II antigens designated DR, DP and DQ. These are expressed in all human haplotypes. The DR subset has been reported to be present in highest concentration (Gorga, J., et al., J. Biol. Chem. 262:16087-16094 (1987)). This is one explanation for our selective isolation of the DR subset over DP and DQ.

The possible contamination of preparations with tissue factor was of concern. It should be noted that HLA-DR was immunochemically purified hence reducing any interference from contaminants. More importantly, preparations of human ovarian carcinoma used to isolate HLA-DR had the same procoagulant activity in the presence or absence of anti-human tissue factor. These findings coupled with the observation that SEA inhibits the procoagulant activity of HLA-DR clearly establish that the procoagulant activity of HLA-DR isolated from human ovarian carcinoma is unrelated to tissue factor.

A number of nonlymphoid cancers such as colorectal (Daar, A. S., et al., J. Immunol. 129:447–449 (1982) and melanoma (Winchester, R. J., Proc. Natl. Acad. Sci. USA. 75:6235–6239 (1978)) have been shown to express the Class II antigens. Basham and Merigan (Basham, T. Y., et al., J. Immunol. 130:1492–1494 (1983)) have observed a five to six-fold increase in the synthesis and expression of HLA-DR in melanoma cells upon stimulation by interferon-gamma. They have therefore suggested that these antigens may be involved in immunologic interactions between the host and the tumor. The molecular mechanisms by which the histocompatibility antigens mediate the immune response in normal and cancer states needs to be delineated. In addition to its immunological function, the class II antigen, HLA-DR also contains procoagulant activity. It is not known if the procoagulant activity of HLA-DR has any role in the immune response.

SPECIFIC DESCRIPTION

Materials and Methods

Human ovarian carcinoma was selected since ovarian tumors have high levels of procoagulant activity and adequate amounts of starting material were available. The procoagulant protein finally isolated had properties different from those ascribed to the other tumor procoagulants. The protein isolated was the DR subset of the Class II major histocompatibility antigens (MHC).

Example 1

Human ovarian tumors were provided by The National Disease Resource Interchange, Philadelphia, Pa. and The Cooperative Human Tissue Network, Columbus, Ohio. All other chemicals were purchased from Sigma Chemical Company, St. Louis, Mo., unless otherwise stated.

Isolation of light mitochondrial fraction. This fraction was isolated according to the modified method (Rozhin, J., et al., Cancer Res. 47:6602–6628 (1987)) of DeDuve et al (DeDuve, C., et al., Biochem J. 60:604–615 (1955)). All isolation procedures were carried out at 4° C. Fresh frozen tumor, 30–40 gm tumor wet weight, was ground in a food processor, suspended in 10 volumes of 25 mM MES buffer pH 6.5 containing 5% sucrose, 0.9% NaCl, 10 mM EDTA, 1 mM Phenylmethylsulfonyl fluoride (PMSF), $10^{-6}$M trans-Epoxysuccinyl-L-leucylamido-(4-guanidino)butane(E-64) and 1 mM leupeptin and homogenized by ten strokes through a Potter-Elvejheim homogenizer. The cell homogenate was passed through a muslin gauze and the filtrate centrifuged at $6700 \times g$ for 7 minutes in a Beckman Ti45 rotor. The pellet containing the nuclear and mitochondrial fraction was resuspended in the MES buffer and the centrifugation repeated at $6700 \times g$ for 7 minutes. The supernatants were pooled and recentrifuged at $15,100 \times g$ for 19 minutes in the same rotor. The resulting pellet, the light mitochondrial fraction, was resuspended in 25 mM Tris-HCl buffer, pH 8.2. CHAPS was added to the suspension to obtain a final concentration of 0.25%.

Isolation of Procoagulant Protein. The light mitochondrial fraction (i.e. plasma membrane plus lysosomal) was applied onto a 1 cm × 30 cm Q-Sepharose (Pharmacia, Piscataway, N.J.) column equilibrated in 25 mM Tris-HCl buffer, pH 7.5, containing 0.25% CHAPS. The column was developed as detailed in reference to FIG. 1a. Activity was quantitated in a newly developed coagulation assay described below. Active fractions were pooled, dialyzed against 10 mM $KH_2PO_4/K_2HPO_4$ buffer pH 7.2 containing 0.25% CHAPS and applied onto a hydroxyapatite (Bio-Rad, Rockville, N.Y.) column equilibrated in the same buffer. Procoagulant activity which eluted with the unbound fraction was dialyzed extensively against distilled water to remove CHAPS and lyophilized. The dried powder was resuspended in a minimal volume of 25 mM Tris-HCl buffer, pH 8.2 and lipid extracted from the preparation by vortexing each ml of reconstituted protein sample with 0.7 ml of LipiFree TM (1, 1,2-Trichlorotriluoro thane; Genex Corporation, Gaithersburg, Md.). The cloudy suspension was centrifuged at $1000 \times g$ for 20 minutes. The aqueous upper layer, containing the procoagulant activity, was carefully siphoned off, applied onto a Mono Q column (Pharmacia) and developed as described in reference to FIG. 1b.

Active fractions analyzed on SDS-PAGE (Laemmli, U. K., Nature (London) 227:680–685 (1970)) were found to have at least four protein bands. The preparation was then electrophoresed in duplicate lanes on SDS-PAGE and the proteins transferred onto an immobilon P membrane. One lane was stained with Coomassie blue and destained to identify the protein bands. All corresponding bands in an unstained lane were excised and assayed for procoagulant activity. This procedure identified proteins with procoagulant activity in the stained lane and were excised for sequence analysis. Sections of membrane which contained no protein were also tested in controls. Protein microsequence analysis was obtained by automated Edman chemistry on an Applied Biosystems gas phase sequenator, Model 470, with on line HPLC (Model 120), a Nelson Analytical chromatography Data System and a 900 A control/data system. Levels below 100 picomoles have been sequenced routinely for proteins transferred by electroblotting to polyvinyl difluoride (PVDF; eg Immobilon P, Millipore Corporation, Burlington, Mass.) membranes.

Lectin Affinity Chromatography. This procedure was as previously described (Roitt, I., et al., Anal. Biochem. 116:53–64 (1985)). Light mitochondrial fraction from human ovarian carcinoma, solubilized in 1% Triton X-100, was applied onto the lectin-Sepharose column equilibrated with 50 mM HEPES buffer pH 7.5 containing 1 mM $CaCl_2$ and 1 mM $MnCl_2$ and washed to remove all unbound protein. Bound protein was eluted with 0.1M methyl alpha-D-mannopyranoside in HEPES buffer, pH 7.5. The eluate was dialyzed extensively against distilled water and lyophilized.

Immunochemical Isolation using Anti-HLA-DR column. Monoclonal antibody to HLA-DR (AMAC, Inc. Westbrook, Me.) was reconstituted in $H_2O$, dialyzed against 0.1M sodium bicarbonate buffer pH 8.3 containing 0.5M NaCl (coupling buffer) and coupled to CNBr-activated Sepharose 4B suspended in the same buffer. The protein isolated from the lectin column was applied to the immunoaffinity column. The column was washed with at least three column volumes to remove unbound protein and bound protein was eluated with 0.1M Glycine/HCl buffer, pH 2.5. Eluted fractions were dialyzed extensively against $H_2O$ and lyophilized. Protein concentration was determined according to the Bradford method (Read, S. M., et al., Anal. Biochem. 116:53-64 (1981)).

Coagulation Assay. Plasma was rendered free of fibrinogen with the aid of ancrod defibrilating enzyme, Sigma Chemical Co., St. Louis, Mo. (Seligson, D., Hematology, Vol III:301 (1980)). The resulting clot was removed and the remaining plasma activated (5 rain, 25° C.) by addition of calcium chloride (6.25 mM final concentration) in the presence or absence of the tumor procoagulant. The reaction was stopped at various timed intervals with the addition of 2.5 mM EDTA (final concentration). Thrombin generated in these assays was measured using S 2238 (H-D-Phenylalanyl-L-pipecoyl-L-arginine-o-nitroanilide dihydrochloride), a thrombin-specific chromogenic substrate (Sandberg, H., et al. Throm. Res. 14:113-124 (1979)). The color generated after addition of S2238 was stopped with 50% acetic acid and absorbance measured in a Bio-Tek EL312 Microplate Reader. The unit of procoagulant activity is defined as the amount of protein required to generate one unit of thrombin per min. For a standard curve, known amounts of thrombin were used to hydrolyze S2238 and the rate of change of optical density per minute versus thrombin concentration was obtained. Rabbit thromboplastin used, under the same conditions, in controls and was found to generate 5.5 units of thrombin per minute per mg protein. By comparison, immunochemically purified HLA-DR generated 435 units of thrombin per min per mg protein. This represents a 79-fold higher activity compared to thromboplastin. Anti-human tissue factor antibody did not have any effect on the procoagulant activity of our preparations of human ovarian carcinoma. The effect of HLA-DR on thrombin generation in commercially available factor-deficient plasmas (Helena Laboratories, Beaumont, Tex.) were also tested.

The Western blot protein transfer procedure is a modification of the Bio-Rad method. All buffers were made with Milli-Q (Millipore Corporation, Burlington, Mass.) grade water. Proteins in a polyacrylamide gel slab were electrically transferred (35 V constant for 16 h) onto an Immobilon P membrane (Millipore) using a Bio-Rad Trans-Blot apparatus and 25 mM Tris, 200 mM glycine, 20% methanol, pH 8.3 as the transfer buffer. The membrane was stained for 15 min with 0.25% Coomassie blue in 50% methanol. The membrane was then destained in 90% methanol.

RESULTS

Initially, the isolation of procoagulant activity was attempted using conventional methods. A plasma membrane enriched fraction was isolated since it was observed that (i) intact tumor cells were able to significantly reduce clotting time in recalcified plasma and (ii) in subcellular fractionation studies the plasma membrane of the human ovarian carcinoma contained more than 85% of the total procoagulant activity (Chelladurai, M., et al., Proc. Am. Ass. Can. Res. 29:68a (1988)). Furthermore, our studies have shown that the expression of procoagulant activity was increased as much as 20,000 fold greater in murine tumor tissues compared to normal cells (Chelladurai, M., et al., Proc. Am. Ass. Can. Res. 29:68a (1988)). The detergent CHAPS was employed to solubilize the light nitochondrial fraction and in buffers for the first ion-exchange chromatography and hydroxyapatite column. Subsequently, all procedures were carried out in the absence of detergent. In order to reduce interference from lipids in the membrane fraction, the material containing procoagulant activity was treated with Lipifree TM. Following the isolation protocol described in the legends to FIGS. 1a and 1b, the protein yields were poor and homogeneity was not achieved. Therefore, the semipurified protein preparation was separated on SDS-PAGE, transferred onto an immobilon P membrane and Coomassie stained to identify the protein bands (FIG. 1c). Two protein bands of 35,000 and 28,000 daltons were found to have procoagulant activity. The corresponding stained bands were then excised and used for sequence analysis. The sequence of the first 12 residues of the 35,000 protein band is shown in FIG. 2. A computer search matched this sequence exactly with the sequence of the major histocompatibility antigen HLA-DR.

In order to verify that the procoagulant activity resided with HLA-DR, the protein was isolated using published methods (Read, S. M., et al., Anal. Biochem. 116:53-64 (1981)). HLA-DR was isolated by lentil lectin affinity chromatography followed by immunoaffinity chromatography. The protein that bound to the anti-HLA-DR monoclonal antibody column had strong procoagulant activity with a specific activity of 435 units/mg protein. This activity was about 79-fold higher than that for rabbit thromboplastin under the same conditions. The procoagulant nature of HLA-DR was verified when authentic HLA-DR expressed the same procoagulant activity reported in this work.

Immunochemically isolated HLA-DR enhanced thrombin generation approximately 20-fold in normal plasma during the first four minutes of incubation of the protein in recalcified plasma (FIG. 3a). The final concentration of HLA-DR in the assay was 115 nM. Thrombin generation was enhanced two-fold with 11.5 nM. Since most coagulation factors are present in plasma at micromolar concentrations or greater (Shapiro, S. S., et al., In Hemostasis and Thrombosis (eds. E. J. W. Bowie and A.A. Sharp), Buttersworth, London. pp 197-236 (1985)), HLA-DR appears to be quite efficient in promoting thrombin generation.

The procoagulant activity of HLA-DR was completely inhibited when preincubated with equimolar concentrations of staphylococcal enterotoxin A (SEA). SEA specifically binds to HLA-DR (Fleischer, B., et al., Cell. Immunol. 120:92-101 (1989)). This inhibition served as the basis for qualifying HLA.

Example 2

Table 1 shows the procoagulant activity of various cell lines in a coagulation assay with plasma free of fibrinogen. The thrombin generated was tested with S2238 as in Example 1 and the absorbance was increased. The same cell lines were tested with SEA and the results are shown in Table 2. The cell lines are various metastatic cell lines. WM 1158 and WM 323 are melanoma cells.

TABLE 1

Effect of SEA on procoagulant Activity of various melanoma cell lines.
Procoagulant Activity of Human Melanoma Cells.

| Cell line | Procoagulant |
| Activity | Units/ml Thrombin |
| --- | --- |
| WM 983.C | 0 |
| WM 983.A | 0 |
| WM 239.A | 9.37 |
| WM 373 | 8.99 |
| WM 1158 | 2.38 |

TABLE 1-continued

Effect of SEA on procoagulant Activity of various melanoma cell lines.

Procoagulant Activity of Human Melanoma Cells.

| Cell line | Procoagulant Activity Units/ml Thrombin |
|---|---|
| WM 1341-D | 1.49 |
| WM 164 | 1.80 |

Of the seven cell lines tested above, only five cell lines had procoagulant activity,

TABLE 2

Effect of Staphylococcal enterotoxin A (SEA) on the procoagulant activity of melanoma cell lines.

| Cell Line | % Reduction of Activity by SEA |
|---|---|
| WM 164 | 0 |
| WM 239.A | 0 |
| WM 1341-D | 0 |
| WM 1158 | 34% |
| WM 373 | 42% |

Delineation of the mechanism of thrombin generation by HLA-DR was attempted. The rate of clotting of Factor VII-deficient plasma was enhanced to an extent similar to normal plasma in the presence of HLA-DR (FIG. 3B). HLA-DR's ability to generate thrombin however was dependent on all coagulant factors of the intrinsic pathway. No activity was observed with individual plasmas deficient in factors XII, XI, X, IX, VIII, or V. It is not clear at this time what mechanism(s) is involved in thrombin generation. These results on the coagulation factor requirement have to be viewed with caution, since congenitally deficient plasma known to contain no biological activity may have immunochemically detectable proteins.

It is intended that the foregoing description be only illustrative of the present invention and that the present invention be limited only by the hereinafter appended claims.

We claim:

1. A method for screening cells for human tumor cells which are metastatic which comprises:

(a) contacting a sample of human cells suspected of containing human tumor cells which are metastatic with a microbial toxin or active subunit of the toxin which selectively binds Human Leukocyte Antigen-DR (HLA-DR);

(b) incubating the toxin or subunit with the HLA-DR to permit the toxin to bind HLA-DR in the sample;

(c) detecting the HLA-DR bound to the toxin or subunit; and (d) correlating the toxin or subunit bound HLA-DR to cells with normal human cells to determine that the cells are metastatic, wherein the tumor cells which are metastatic exhibit higher HLA-DR as compared to HLA-DR in the normal human cells.

2. A method for screening cells for human tumor cells which are metastatic which comprises:

(a) contacting a sample of cells suspected of containing tumor cells which are metastatic with a microbial toxin or active subunit of the toxin which selectively binds Human Leukocyte Antigen-DR (HLA-DR);

(b) incubating the toxin with the HLA-DR to permit the microbial toxin or subunit to bind the HLA-DR in the sample;

(c) detecting the HLA-DR bound to the toxin or subunit; and (d) correlating the bound HLA-DR to cells which are non-tumor cells to determine that the cells are metastatic, wherein the tumor cells which are metastatic exhibit higher HLA-DR as compared to HLA-DR in the normal human cells as determined by the binding of the HLA-DR with the toxin or subunit.

3. The method of claim 2 wherein the toxin is selected from the group consisting of *Staphylococcus aureus* enteroxin A, B, C1, C2, C3, D and E, Toxic Shock Syndrome bacterial toxin, *Streptococcus pyrogenes* A and C, *Staphylococcus aureus* exfoliating toxins A and B and active subunits of the toxins which selectively bind the HLA-DR.

4. The method of claim 2 wherein the test is an assay which determines an amount of toxin bound HLA-DR.

5. The method of claim 2 wherein the test is a blood coagulation assay in a blood serum and wherein the toxin bound to the HLA-DR inhibits the rate of blood coagulation in the assay as compared to tumor cells with HLA-DR.

6. The method of claim 2 wherein the test is a blood coagulation assay with blood plasma which is free of fibrinogen and wherein the HLA-DR induces thrombin in the blood plasma which is detected.

7. The method of claim 2 wherein the thrombin is detected by a colorimetric assay.

8. The method of claim 2 wherein a control sample of a normal tissue with a normal level of HLA-DR is tested along with the test sample.

9. The method of claim 7 wherein the control sample is a blood serum which has a normal prothrombin and activated partial thrombin clotting time.

10. The method of claim 2 wherein the toxin is *Staphylococcus aureus* enterotoxin A.

11. The method of claim 6 wherein the fibrinogen is removed with a clotting agent which selectively reacts with fibrinogen to convert the fibrinogen to fibrin which is removed from the plasma.

12. The method of claim 11 wherein the clotting agent is ancrod.

13. The method of claim 1 wherein the sample is blood serum.

14. The method of claim 13 wherein a control sample of normal serum is tested along with the sample of the blood serum suspected of containing human tumor cells.

* * * * *

UNITED STATES PATENT AND TRADEMARK OFFICE
CERTIFICATE OF CORRECTION

PATENT NO. : 5,378,607

DATED : January 3, 1995

INVENTOR(S) : Mohanathasan Chelladurai, Kenneth V. Honn and Daniel A. Walz

It is certified that error appears in the above—identified patent and that said Letters Patent is hereby corrected as shown below:

Column 1, line 14, "For" should be --for--.

Column 2, line 1, the semicolon ":" after "the" should be deleted.

Column 3, line 10, after "FIG." insert -- 3 --.

Column 3, lines 12 and 13, after "nothing" and before "which", -- □ -- should be inserted.

Column 7, line 7, "(5 rain" should read --(5 min"--.

Column 7, lines 63 and 64, "nitochondrial" should be --mitochondrial--.

Column 9, line 45, "activity," should read --activity.--.

Column 11, lines 11 and 12 (Claim 3), "enteroxin" should be --enterotoxin--.

Signed and Sealed this

Ninth Day of May, 1995

Attest:

Attesting Officer

BRUCE LEHMAN

Commissioner of Patents and Trademarks

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 12
        ( B ) TYPE: Amino Acid
        ( C ) STRANDEDNESS: Single
        ( D ) TOPOLOGY: Unknown ( i i ) MOLECULE TYPE:
        ( A ) DESCRIPTION: Polypeptide ( i i i ) HYPOTHETICAL: No ( i v ) ANTI-SENSE: No ( v i ) ORIGINAL SOURCE:
        ( A ) ORGANISM: HLA DR and Human Ovarian Carcinoma
        ( B ) STRAIN: N/A
        ( C ) INDIVIDUAL ISOLATE: N/A
        ( G ) CELL TYPE: Human ( i x ) FEATURE:
        ( A ) NAME/KEY: Partial polypeptide of HLA-DR
        ( B ) LOCATION: N/A
        ( C ) IDENTIFICATION METHOD: Sequencing
        ( D ) OTHER INFORMATION: Polypeptide ( x i ) SEQUENCE DESCRIPTION: SEQ ID NO:1:

Ile  Lys  Glu  Glu  His  Val  Ile  Ile  Gln  Ala  Glu  Phe
                                5                              10